(12) United States Patent
Yu et al.

(10) Patent No.: US 11,389,947 B2
(45) Date of Patent: Jul. 19, 2022

(54) SEMI-ACTIVE RIGID-FLEXIBLE COUPLING EXOSKELETON BASED ON SINGLE-LOOP BIDIRECTIONAL DAMPING REGULATOR

(71) Applicant: UNIVERSITY OF SHANGHAI FOR SCIENCE AND TECHNOLOGY, Shanghai (CN)

(72) Inventors: Hongliu Yu, Shanghai (CN); Xiaoming Wang, Shanghai (CN); Zhewen Zhang, Shanghai (CN); Qiaoling Meng, Shanghai (CN)

(73) Assignee: UNIVERSITY OF SHANGHAI FOR SCIENCE AND TECHNOLOGY, Shanghai (CN)

(*) Notice: Subject to any disclaimer, the term of this patent is extended or adjusted under 35 U.S.C. 154(b) by 0 days.

(21) Appl. No.: 17/278,359

(22) PCT Filed: Dec. 10, 2020

(86) PCT No.: PCT/CN2020/135125
§ 371 (c)(1),
(2) Date: Mar. 22, 2021

(87) PCT Pub. No.: WO2022/011941
PCT Pub. Date: Jan. 20, 2022

(65) Prior Publication Data
US 2022/0143808 A1 May 12, 2022

(30) Foreign Application Priority Data

Jul. 14, 2020 (CN) .................. 202010674616.2
Jul. 14, 2020 (CN) .................. 202010675494.9

(51) Int. Cl.
*B25J 9/00* (2006.01)
*A61B 5/107* (2006.01)

(52) U.S. Cl.
CPC .......... *B25J 9/0006* (2013.01); *A61B 5/1071* (2013.01)

(58) Field of Classification Search
CPC ............................ B25J 9/0006; A61B 5/1071
See application file for complete search history.

(56) References Cited

U.S. PATENT DOCUMENTS

2004/0201185 A1  10/2004  Beck

FOREIGN PATENT DOCUMENTS

| CN | 103260576 A | 8/2013 |
|---|---|---|
| CN | 107035808 A | 8/2017 |

(Continued)

OTHER PUBLICATIONS

International Search Report in PCT/CN2020/135125, issued by ISA, dated Mar. 25, 2021.

(Continued)

*Primary Examiner* — Jerrah Edwards
*Assistant Examiner* — Aren Patel
(74) *Attorney, Agent, or Firm* — Zhu Lehnhoff LLP

(57) ABSTRACT

This invention discloses a semi-active rigid-flexible coupling exoskeleton based on a single-loop bidirectional damping regulator and relates to a power assisting mechanism in the field of robots, the exoskeleton including a waist assembly, a leg assembly, and a hydraulic damping regulator; the hydraulic damping regulator includes a cylinder body, a titanium alloy sleeve, a cylinder head, a piston, an extension assisting spring, an oil injection port plug, a staggered channel-type valve body, a valve body sealing seat, a valve body-end bevel gear, an angle sensor, a motor fixing seat, a DC servo motor, a coupler, and a motor-end bevel gear. According to the invention, two modes of power assistance or damping regulation, i.e., a heavy-object-carrying mode and a walking-with-load mode, can be enabled;

(Continued)

the heavy-object-carrying mode supports carrying from a higher to a lower position and the other way around, characterized by good applicability; moreover, the knee joint can be assisted when naturally bending in a stooping state; a semi-active torque adjusting system is formed with a hydraulic damper and a spring, with the magnitude of assistance and damping force adjustable; also, this invention features a light weight and good man-machine coupling.

6 Claims, 8 Drawing Sheets

(56) References Cited

FOREIGN PATENT DOCUMENTS

| | | | |
|---|---|---|---|
| CN | 108071732 | A | 5/2018 |
| CN | 108266483 | A | 7/2018 |
| CN | 111110410 | A | 5/2020 |
| CN | 111166540 | A | 5/2020 |
| CN | 111779788 | A | 10/2020 |
| CN | 111805513 | A | 10/2020 |
| JP | 2018012148 | A | 1/2018 |

OTHER PUBLICATIONS

Written Opinion of the International Search Report in PCT/CN2020/135125, issued by ISA, dated Mar. 25, 2021.

SEMI-ACTIVE RIGID-FLEXIBLE COUPLING EXOSKELETON BASED ON SINGLE-LOOP BIDIRECTIONAL DAMPING REGULATOR

TECHNICAL FIELD

This invention relates to a power assisting mechanism in the field of robots, and more particularly, to a semi-active rigid-flexible coupling exoskeleton based on a single-loop bidirectional damping regulator.

BACKGROUND

China has a large number of practitioners in the industries such as transportation, logistics, construction, and manufacturing, a significant portion of professions require long-term repetitive labor, resulting in limb fatigue damage, especially the damage to the waist and knees. An exoskeleton robot, an intelligent wearable device that integrates bionics and ergonomics, simulates the motion of a human body and enhances the athletic capability of the human body, and can improve the performance of the human body in some aspects such as walking durability and load-bearing capability. In the prior art, waist and knee assisting exoskeletons have two major types, namely, active assisting exoskeletons and passive assisting exoskeletons. The active power assisting exoskeleton assists upper body movement or flexion and extension of the knee joint of a human body by controlling the direction and the torque of rotation of a power assisting motor provided at a joint. The driving system of the solution features a large mass, high energy consumption, short endurance, and poor man-machine coupling. The passive power assisting exoskeleton mainly adopts springs or elastic cables to store energy when a person stoops or bends his knees, and releases energy when the person stands up or stretches his knees, so that an assisting effect is achieved. The system of the solution features a simple structure, a small mass, and good man-machine coupling, but is defective in that the assisting force is not adjustable.

Application No. 201911255477.3 provides a passive waist power assisting exoskeleton based on spring energy storage. The spring is controlled by a special-shaped wheel rotating along with the stooping/standing-up action of a human body to compress or extend, stores energy when a user stoops, and releases energy when the user stands up, to provide power assistance for the user in lifting and carrying a load. The biggest problem of the solution is that the assisting force size is not adjustable, and only applicable to the situation where the user carries a load from a higher position to a lower position.

Application No. 201910402215.9 provides a waist power assisting exoskeleton that combines both active and passive modes, wherein a curling part is designed to convert gravitational potential energy into elastic potential energy when a user stoops. In comparison with Application No. 201911255477.3, in addition to using the stored elastic potential energy, the solution uses a motor drive to actively provide power assistance when the user stands up and carries a load. However, in this solution, the system consumes energy greatly, even though the battery power consumption can be reduced by reducing the work of a driving unit to lower the power supply for the driving unit. Moreover, the waist power assisting exoskeletons provided by the above two applications ignore the natural bending when the human body stoops, as a result, the waist power assisting and the knee power assisting cannot be enabled at the same time.

Application No. 201710736309.0 provides a knee joint walking assisting robot, wherein a hydraulic damper is provided at a knee joint, and a flow adjusting device is provided on a hydraulic lever, so that different damping forces are enabled in different walking states, but bending and extension damping forces cannot be independently adjusted; when hydraulic oil in a cavity is compressed in the movement the knee joint, a motor is imposed a heavy axial load, hence the motor is likely to be out of step and cannot reach a specified position in the adjustment process, which seriously affects the performance of the knee joint damping regulation.

Therefore, those skilled in the art have been committed to developing a semi-active rigid-flexible coupling exoskeleton based on a single-loop bidirectional damping regulator, to solve the problems of high energy consumption, short endurance, poor man-machine coupling, and non-adjustable power assistance in the prior art.

SUMMARY OF THE INVENTION

In view of the above-mentioned defects in the prior art, it's an object of this invention to solve the technical problems of high energy consumption, short endurance time, poor man-machine coupling, and non-adjustable power assistance in the prior art.

Different properties can be seen in the hydraulic damping force along with the change of the velocity of a hydraulic oil flow, the damping is in linear relation to the velocity when the flow is slow, i.e., a laminar flow, and in nonlinear relation when the flow is fast, i.e., a turbulent flow. According to such properties, the damping force at different velocities can be adjusted by changing a flow area of the hydraulic oil and thus changing the velocity of the hydraulic oil flow to generate turbulence, whereby a quick adaptation and control of the damping torque is enabled. In this case, the required energy consumption is far lower than the energy consumed when the same damping force is provided by a motor drive. The semi-active rigid-flexible coupling exoskeleton based on the single-loop bidirectional damping regulator is constructed on the basis of a spring-hydraulic damper.

To achieve the above object, the invention provides a semi-active rigid-flexible coupling exoskeleton based on a single-loop bidirectional damping regulator, including:
  a waist assembly and a leg assembly; and
  a hydraulic damping regulator comprising a cylinder body, a titanium alloy sleeve, a cylinder head, a piston, an extension assisting spring, an oil injection port plug, and a flow pre-regulating component, the flow pre-regulating component comprising a staggered channel-type valve body, a valve body sealing seat, a valve body-end bevel gear, an angle sensor, a motor fixing seat, a DC servo motor, a coupler, and a motor-end bevel gear;
  wherein,
  the titanium alloy sleeve is coaxially nested inside the cylinder body;
  the cylinder head is in threaded connection with an upper end of the cylinder body;
  the piston includes an upper piston rod, a piston body, and a hollow lower piston rod;
  the upper piston rod penetrates through the cylinder head;
  the hollow lower piston rod penetrates through a lower end of the cylinder body;
  the piston body moves up and down in the cylinder body and divides an inner cavity of the cylinder body into an upper cavity and a lower cavity;

an upper cavity oil hole and a lower cavity oil hole are drilled into both ends of the inner cavity of the cylinder body and correspondingly into the titanium alloy sleeve, respectively;

an oil injection port is formed in a cylinder wall of the cylinder body, and an oil channel communicating the oil injection port with the upper cavity oil hole and the lower cavity oil hole forms a hydraulic oil circuit;

the oil injection port plug is in threaded connection with the oil injection port;

a special-shaped shaft is provided on one side of the staggered channel-type valve body;

the special-shaped shaft is coaxially matched with a hole formed in the valve body sealing seat, the valve body-end bevel gear, and the angle sensor sequentially, and the valve body-end bevel gear is fixed with the angle sensor and the special-shaped shaft through a set screw;

the valve body sealing seat and the motor fixing seat are fixed on a side wall of the cylinder body through screws;

the DC servo motor is fixed on the motor fixing seat through threads, and an output end of the motor is connected with the motor-end bevel gear through the coupler; and the valve body-end bevel gear is geared with the motor-end bevel gear.

Furthermore, the hydraulic damping regulator has two different structures corresponding to deployments at a waist and a knee, respectively namely, a knee hydraulic damping regulator and a waist hydraulic damping regulator.

Furthermore, the extension assisting spring in the knee hydraulic damping regulator is placed inside the lower cavity of the cylinder body, and the extension assisting spring in the waist hydraulic damping regulator is placed inside the upper cavity of the cylinder body.

Furthermore, a valve recess and two sector recesses intersecting the upper cavity oil hole and the lower cavity oil hole are formed in the side wall of the cylinder body, so that hydraulic oil from the oil holes can flow into the sector recesses without generating convection impact between channels in the staggered channel-type valve body.

Furthermore, radius angles of the two sector recesses are 55° and 150°, respectively.

Furthermore, the staggered channel-type valve body is provided with a first oil channel and a second oil channel, and axes of the two oil channels are non-coplanar straight lines, so that the two oil channels do not influence each other and form an angle; the angle is configured such that the axes intersect at a point on an edge line of the staggered channel-type valve body at a pair of their ends and form an angle of 27.5° at the other pair of their ends when the axes of the two oil channels are projected on an end face of the staggered channel-type valve body; a circle of bulges is provided on either end face of the staggered channel-type valve body to reduce a contact area of the staggered channel-type valve body with the cylinder body and the valve body sealing seat, respectively, and the staggered channel-type valve body is placed in the valve recess; one-way valves are provided in the first oil channel and the second oil channel in different directions, respectively.

Furthermore, the DC servo motor is geared with the motor-end bevel gear through the valve body-end bevel gear to adjust a rotation angle of the staggered channel-type valve body, flow areas of the first oil channel and the second oil channel in the staggered channel-type valve body are changed through a fit clearance between either the first oil channel or the second oil channel in the staggered channel-type valve body and the sector recess, so that a flow in the upper cavity and the lower cavity of the cylinder body are changed, and an angle sensor is provided at a shaft end of the valve to enable complete closed-loop control of the DC servo motor.

Furthermore, the waist assembly comprises: a waist belt, a shoulder belt, a waist fixing seat, a piston rod connecting block, a pulley component and a Bowden cable; the waist belt and the shoulder belt are made of flexible materials, and a front end of the shoulder belt passes around a human body to fixedly connect the waist belt; the waist belt fixing seat is made of a rigid material, and a lower end of the waist belt fixing seat is fixedly connected with the waist belt through a screw;

the leg assembly comprises a thigh lever, a thigh strap, a leg lever connecting member, a shank lever, a shank strap, and a foot plate; an upper end of the thigh lever is coaxially connected with the lower end of the waist belt at a hip joint of the human body, so that the hip joint has freedom of rotation; the thigh strap penetrates through a square through hole formed in a middle end of the thigh lever for fixing the thigh lever to a thigh of the human body; the shank strap penetrates through a square through hole formed in a middle end of the shank lever for fixing the shank lever and a shank of the human body; a lower end of the shank lever is coaxially connected with the foot plate, so that an ankle joint has freedom of rotation.

Furthermore, in the waist assembly, the pulley component includes a pulley fixing seat, a first pulley, and a second pulley; the pulley fixing seat is fixed at a rear end of the shoulder belt through a screw; the first pulley and the second pulley are symmetrically arranged on two sides of an interior of the pulley fixing seat; the piston rod connecting block is coaxially connected with the upper piston rod in the waist hydraulic damping regulator, and the piston rod connecting block is provided with a first notch, the Bowden cable penetrates through the first notch of the piston rod connecting block and penetrates through the first pulley and the second pulley, respectively, to fixedly connect with left and right sides of the shoulder belt, respectively.

Furthermore, in the leg assembly, the leg lever connecting member comprises a hydraulic cylinder rotary seat, a first end cover, a leg lever bearing, a second end cover, a third end cover, and a piston rod bearing; the hydraulic cylinder rotary seat is composed of a cylinder with a bulge and a hollow cylinder; the cylinder with the bulge is coaxially matched with the middle end of the thigh lever; the first end cover is fixed at a lower end of the thigh lever through a screw and axially fixes the hydraulic cylinder rotary seat through the bulge on the cylinder with the bulge; the hollow cylinder is fixedly connected with a bottom end of the knee hydraulic damping regulator; the hollow lower piston rod passes through the hollow cylinder to move up and down; a second notch is formed at an upper end of the shank lever, and the shank lever is installed in the second notch; the leg lever bearing is installed in a through hole in the lower end of the thigh lever and is coaxially matched with the upper end of the shank lever; the second end cover and the third end cover are fixed on left and right sides of a joint of the thigh lever and the shank lever through screws, respectively, to provide an axial fixation; a special-shaped shaft is provided at a rear part of the upper end of the shank lever, and a tail end of the special-shaped shaft is provided with a thread; the upper piston rod of the knee hydraulic damping regulator is coaxially matched with the special-shaped shaft through the piston rod bearing, and levers are axially fixed through the thread at the tail end of the special-shaped shaft and a nut.

The invention is advantageous at least in that:
1. two modes of power assistance or damping regulation, i.e., a heavy-object-carrying mode and a walking-with-load mode, can be enabled;
2. the heavy-object-carrying mode supports carrying from a higher to a lower position and the other way around, characterized by good applicability; moreover, the knee joint can be assisted when naturally bending in a stooping state;
3. a semi-active torque adjusting system is formed with a hydraulic damper and a spring, with the magnitude of assistance and damping force adjustable;
4. the flexible-rigid coupling exoskeleton features a light weight and good man-machine coupling;
5. the bidirectional independent control of hydraulic damping is enabled by only one motor, and the damping regulation is continuous; compared with a hydraulic damping cylinder structure controlled by two motors, one motor control enables a smaller size, a reduced weight, and lower power consumption for the mechanism;
6. the axial load acting on the motor in the damping cylinder can be effectively avoided, and the possibilities of motor out-of-step and damping regulation failure caused by an overlarge load are avoided; a large tangential force can be effectively prevented when the hydraulic oil flows out of the hydraulic oil channel and directly impacts the valve body in convection, the torque required by the motor for controlling the valve to rotate is greatly reduced, the power consumption is reduced, and the control performance of the motor is improved;
7. the structure is delicate and easy to manufacture.

The concept, specific structure, and technical effects of this invention will be further described with reference to the accompanying drawings to fully teach the object, features, and effects of this invention.

DETAILED DESCRIPTION OF THE PREFERRED EMBODIMENTS

Figure 1:
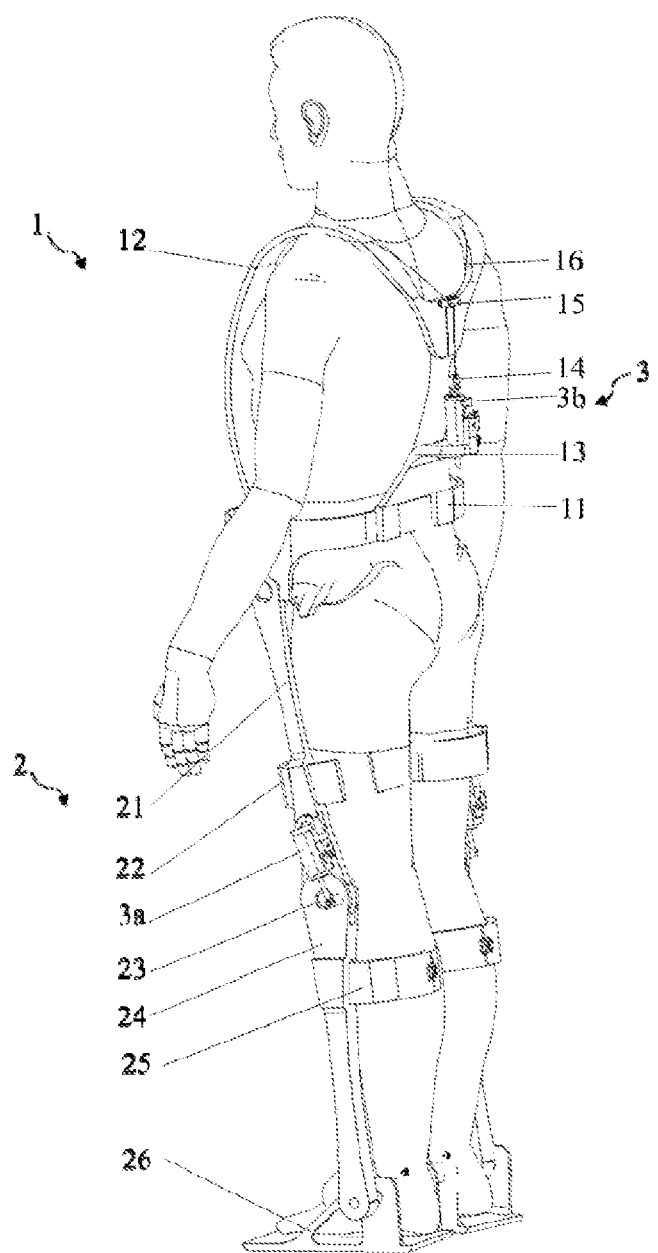
FIG. 1 shows a semi-active rigid-flexible coupling exoskeleton based on a single-loop bi-directional damping regulator worn on a human body according to an embodiment of this invention.

A number of preferred embodiments of this invention will be described with reference to the accompanying drawings to provide a fuller and easier understanding of this invention. This invention may be embodied in many different ways and should not be construed as limited to the embodiments set forth herein.

In the drawings, structurally identical components are denoted by the same reference signs, and structurally or functionally similar components are denoted by like reference signs throughout. The size and thickness of each component shown in the drawings are arbitrarily shown, and the invention is not limited to the shown size and thickness for each component. For clarity of illustration, the thickness of some components may be exaggerated where appropriate.

The semi-active rigid-flexible coupling exoskeleton based on the single-loop bidirectional damping regulator of this invention is described in detail below with reference to the accompanying drawings and embodiments to make the technical means, inventive features, object, and effects enabled by this invention readily apparent.

Figure 2:
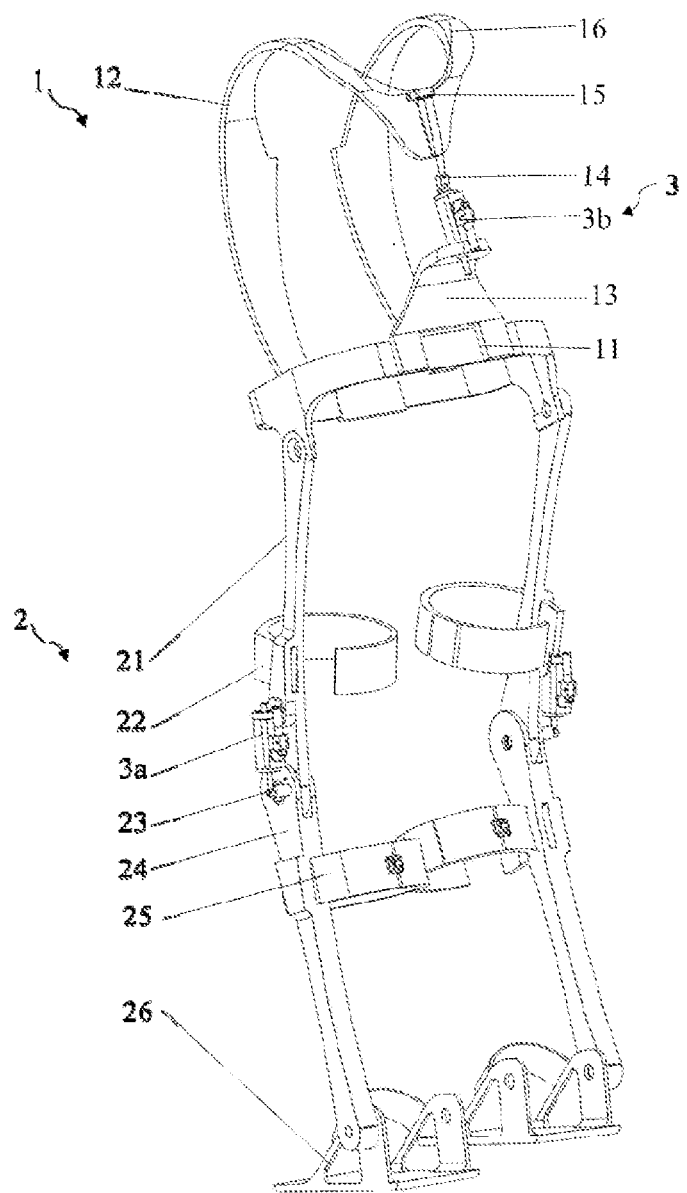
FIG. 2 is an overall view of the exoskeleton according to an embodiment of this invention.

FIG. 1 shows the exoskeleton worn on a human body.
FIG. 2 is an overall view of the exoskeleton.

As shown in FIGS. 1 and 2, the semi-active rigid-flexible coupling exoskeleton based on the single-loop bidirectional damping regulator provided by the invention includes:

a waist assembly 1, including a waist belt 11, a shoulder belt 12, a waist fixing seat 13, a piston rod connecting block 14, a pulley component 15, and a Bowden cable 16, wherein the waist belt 11 and the shoulder belt 12 are made of flexible materials, and a front end of the shoulder belt 12 passes around a human body to be fixedly connected with the waist belt 11; the waist belt fixing seat 13 is made of a rigid material, and a lower end of the waist belt fixing seat 13 is fixedly connected with the waist belt 11 through screws;

a leg assembly 2, including a thigh lever 21, a thigh strap 22, a leg lever connecting member 23, a shank 24, a shank strap 25, and a foot plate 26; wherein an upper end of the thigh lever 21 is coaxially connected with the lower end of the waist belt 11 at a hip joint of the human body, so that the hip joint has freedom of rotation; the thigh strap 22 penetrates through a square through hole formed in a middle end of the thigh lever 21 for fixing the thigh lever 21 to a thigh of the human body; the shank strap 25 penetrates through a square through hole formed in a middle end of the shank lever 24 for fixing the shank lever 24 to a shank of the human body; a lower end of the shank lever 24 is coaxially connected with the foot plate, so that an ankle joint has freedom of rotation; and a hydraulic damping regulator 3, includes a cylinder body 31, a titanium alloy sleeve 32, a cylinder head 33, a piston 34, an extension assisting spring 35, an oil injection port plug 38, and a flow pre-regulating component, the flow pre-regulating component including a staggered channel-type valve body 39, a valve body sealing seat 310, a valve body-end bevel gear 311, an angle sensor 312, a motor fixing seat 313, a DC servo motor 314, a coupler 315, and a motor-end bevel gear 316.

Figure 3:
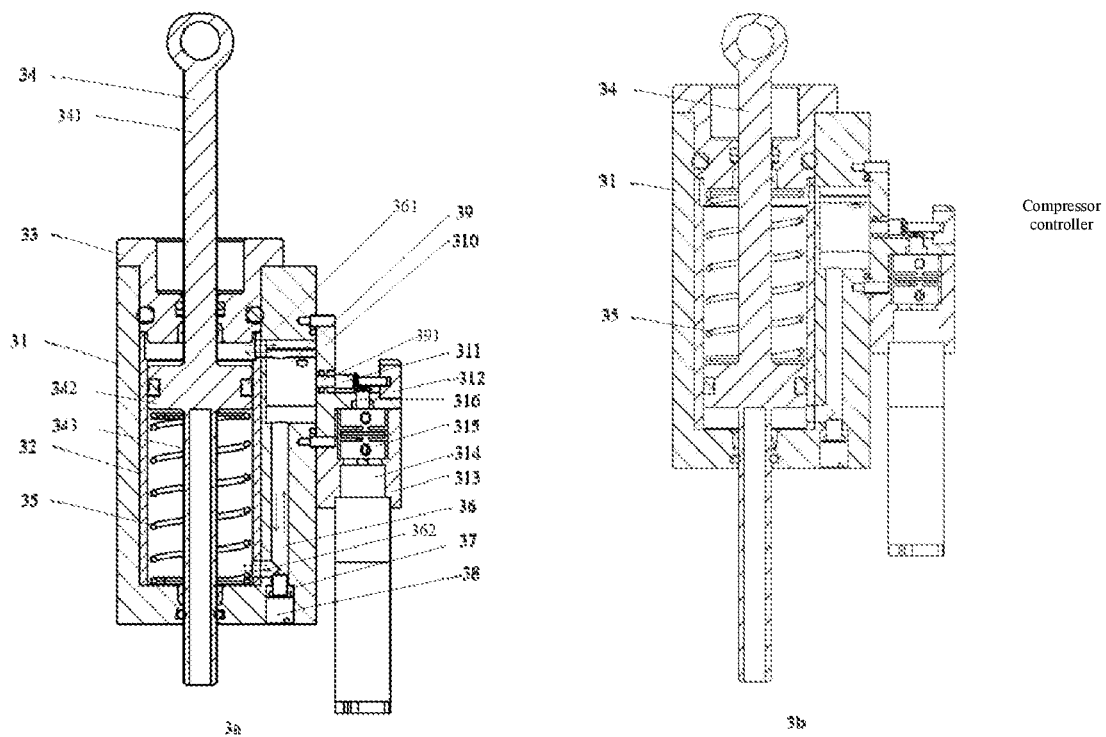
FIG. 3 is a cross-sectional view of the hydraulic damping regulator according to an embodiment of this invention.

FIG. 3 is a cross-sectional view of the hydraulic damping regulator.

As shown in FIG. 3, the hydraulic damping regulator 3 has two different structures corresponding to deployments at a waist and a knee, respectively namely, a knee hydraulic damping regulator 3a and a waist hydraulic damping regulator 3b.

The knee hydraulic damping regulator 3a and the waist hydraulic damping regulator 3b have the following structural characteristics in common, that is, the titanium alloy sleeve 32 is coaxially nested inside the cylinder body 31; the cylinder head 33 is in threaded connection with an upper end of the cylinder body 31; the piston 34 includes an upper piston rod 341, a piston body 342, and a hollow lower piston rod 343; the upper piston rod 341 penetrates through the cylinder head 33, and the upper piston rod 341 is in sealed and movable connection with the cylinder head 33 through a sealing ring and a guide sleeve; the hollow lower piston rod 343 penetrates through a lower end of the cylinder body 31, and the hollow lower piston rod 343 is in sealed and movable connection with the lower end of the cylinder body 31 through a sealing ring and a guide sleeve; the piston body 342 moves up and down in the cylinder body 31 and divides an inner cavity of the cylinder body into an upper cavity and a lower cavity; an upper cavity oil hole 361 and a lower cavity oil hole 362 are drilled into both ends of the inner cavity of the cylinder body 31 and correspondingly into the titanium alloy sleeve 32, respectively; an oil injection port 37 is formed in a cylinder wall of the cylinder body 31, and an oil channel communicating the oil injection port with the upper cavity oil hole 361 and the lower cavity oil hole 362 forms a hydraulic oil circuit 36; the oil injection port plug 38 is in threaded connection with the oil injection port 37, and a sealing ring is provided therebetween to ensure sealing performance. A special-shaped shaft 391 is provided on one side of the staggered channel-type valve body 39; the special-shaped shaft 391 is coaxially matched with a hole formed in the valve body sealing seat 310, the valve body-end bevel gear 311, and the angle sensor 312 sequentially, and the valve body-end bevel gear 311 is fixed with the angle sensor 312 and the special-shaped shaft 391 through a set screw; the valve body sealing seat 310 and the motor fixing seat 313 are fixed on a side wall of the cylinder body 31 through screws; the DC servo motor 314 is fixed on the motor fixing seat 313 through threads, and an output end of the motor is connected with the motor-end bevel gear 316 through the coupler 315; the valve body-end bevel gear 311 is geared with the motor-end bevel gear 316. A sealing ring is provided between the cylinder body 31 and the valve body sealing seat 310, and a sealing ring is provided between the valve body sealing seat 310 and the staggered channel-type valve body 39, so that the sealing performance of the hydraulic cylinder is guaranteed.

Figure 11:
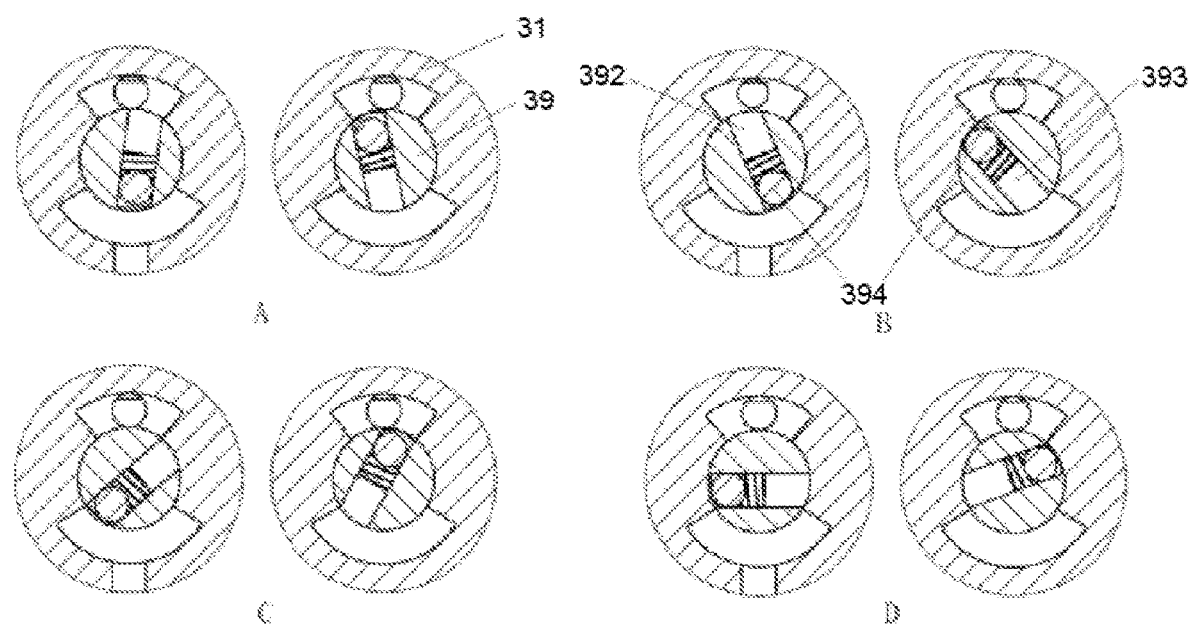
FIG. 11 is a schematic diagram showing various states of the staggered channel-type valve body according to an embodiment of this invention.

In FIG. 11, each state of the staggered channel-type valve body is schematically shown.

In FIG. 4A, the staggered channel-type valve body 39 is in an initial state in which both a flexion oil channel 392 and an extension oil channel 393 coincide with the sector recess 312, and hydraulic oil can be unidirectionally circulated in the flexion oil channel 392 and the extension oil channel 393, respectively.

In FIG. 4B, the staggered channel-type valve body 39 is rotated counterclockwise to an angle of 25° by the DC servo motor 314, the flexion oil channel 392 and the sector recess 320 remain coincident, and the extension oil channel 393 and the sector recess are gradually staggered to a completely closed state.

In FIG. 4C, the staggered channel-type valve body 39 is rotated clockwise from the initial state to an angle of 30°, the flexion oil channel 392 and the sector recess 320 are gradually staggered to the completely closed state, and the extension oil channel 393 and the sector recess 312 remain coincident.

In FIG. 4D, as the staggered channel-type valve body 39 continues to rotate clockwise by 30° from the state shown in FIG. 4C, the flexion oil channel 392 and the sector recess 312 remain completely closed, and the extension oil channel 393 and the sector recess 312 are gradually staggered to the completely closed state.

When the knee joint is in flexion, the piston 34 moves downwards under the action of gravity, the extension assisting spring 35 is compressed to store energy, hydraulic oil enters the hydraulic loop 36 through the lower cavity oil hole 362 to reach the sector recess 320, the staggered channel-type valve body 39 rotates to a preset angle under the driving of the DC servo motor 314, a one-way valve 394 in the extension oil channel 393 closes, and a flow area of the hydraulic oil is changed by changing an area where the flexion oil channel 392 overlaps the sector recess 320, so that the damping force borne by the knee joint during flexion is changed.

When the knee joint is in extension, the energy stored by the extension assisting spring 35 is released to provide assistance for the upward movement of the piston 34, hydraulic oil enters the sector recess 312 through the lower cavity oil hole 361, the staggered channel-type valve body 39 rotates to a preset angle under the driving of the DC servo motor 314, the one-way valve 394 in the flexion oil channel 392 closes, and a flow area of the hydraulic oil is further changed by changing an area where the extension oil channel 393 overlaps the sector recess 312, so that the damping force borne by the knee joint in extension is changed.

The knee hydraulic damping regulator 3a differs from the waist hydraulic damping regulator 3b in the following structural characteristics, that is, the extension assisting spring 35 in the knee hydraulic damping regulator 3a is disposed in the lower cavity of the cylinder body 31, and the extension assisting spring 35 in the waist hydraulic damping regulator 3b is disposed in the upper cavity of the cylinder body 31.

Figure 4:
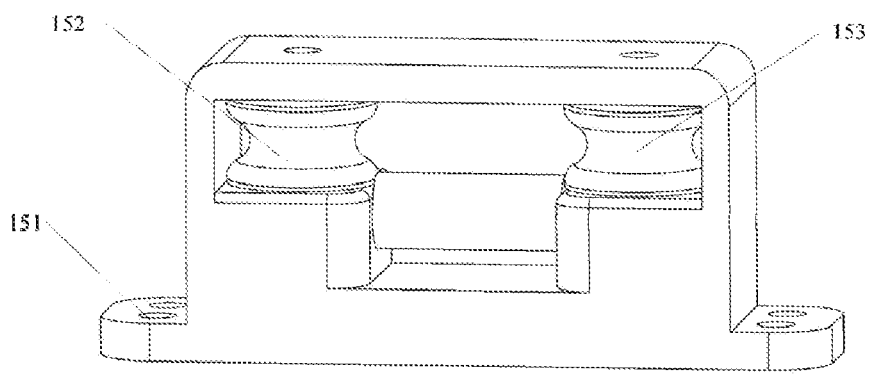
FIG. 4 is a schematic diagram showing a structure of a pulley component according to an embodiment of this invention.

FIG. 4 is a schematic diagram showing the structure of a pulley component.

As shown in FIGS. 1, 2, 3, and 4, in the waist assembly, the pulley component 15 includes a pulley fixing seat 151, a first pulley 152, and a second pulley 153; the pulley fixing seat 151 is fixed at a rear end of the shoulder belt 12 through a screw; the first pulley 152 and the second pulley 153 are symmetrically arranged on two sides of an interior of the pulley fixing seat 151; the piston rod connecting block 14 is coaxially connected with the upper piston rod 341 in the waist hydraulic damping regulator 3b, and the piston rod connecting block 14 is provided with a first notch, the Bowden cable 16 penetrates through the first notch of the piston rod connecting block 14 and penetrates through the first pulley 152 and the second pulley 153, respectively, to fixedly connect with left and right sides of the shoulder belt 12, respectively.

Figure 5:
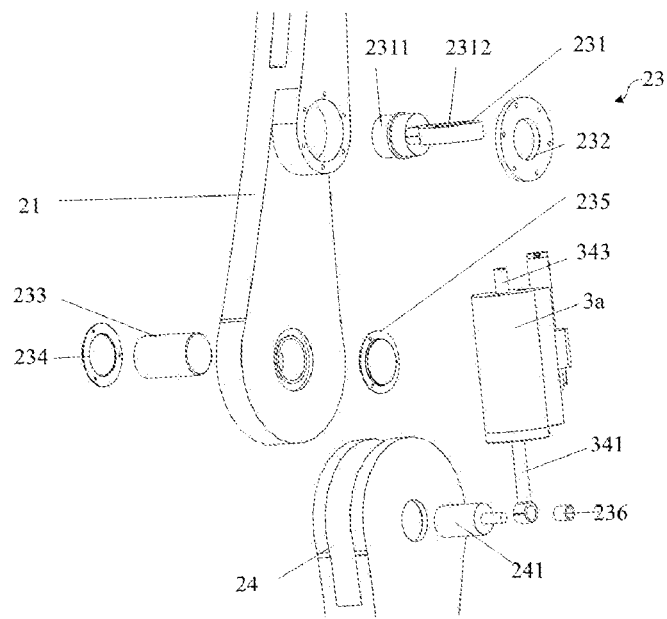
FIG. 5 is a schematic diagram showing a structure of a leg lever connection according to an embodiment of this invention.

FIG. 5 is a schematic diagram showing a structure of a leg lever connection.

As shown in FIGS. 1, 2, 3, and 5, in the leg assembly 2, the leg lever component 23 includes a hydraulic cylinder rotary seat 231, a first end cover 232, a leg lever bearing 233, a second end cover 234, a third end cover 235, and a piston rod bearing 236. The hydraulic cylinder rotary seat 231 is composed of a cylinder with a bulge 2311 and a hollow cylinder 2312; the cylinder with the bulge 2311 is coaxially matched with the middle end of the thigh lever 21; the first end cover 232 is fixed at a lower end of the thigh lever 21 through a screw and axially fixes the hydraulic cylinder rotary seat 231 through the bulge on the cylinder with the bulge 2311; the hollow cylinder 2312 is fixedly connected with a bottom end of the knee hydraulic damping regulator 3a; the hollow lower piston rod 343 passes through the hollow cylinder 2312 to move up and down; a second notch is formed at an upper end of the shank lever 24, and the shank lever 24 is installed in the second notch; the leg lever bearing 233 is installed in a through hole in the lower end of the thigh lever 21 and is coaxially matched with the upper end of the shank lever 24; the second end cover 234 and the third end cover 235 are fixed on left and right sides of a joint of the thigh lever 21 and the shank lever 24 through screws, respectively, to provide an axial fixation; a special-shaped shaft 241 is provided at a rear part of the upper end of the shank lever 24, and a tail end of the special-shaped shaft 241 is provided with a thread; the upper piston rod 341 of the knee hydraulic damping regulator 3a is coaxially matched with the special-shaped shaft 241 through the piston rod bearing 236, and levers are axially fixed through the thread at the tail end of the special-shaped shaft 241 and a nut.

Figure 6:
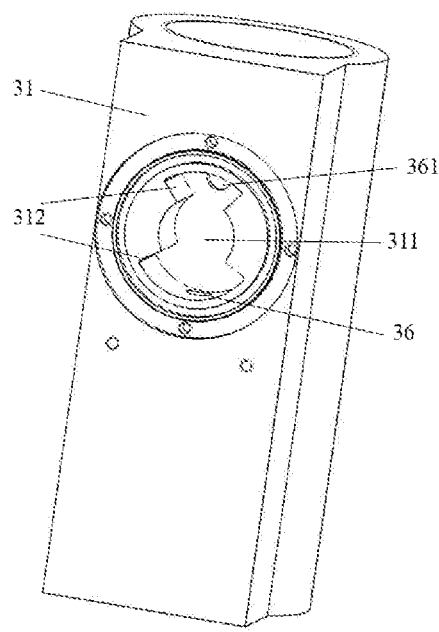
FIG. 6 is a schematic diagram showing a structure of a cylinder body according to an embodiment of this invention.

FIG. 6 is a schematic diagram showing a structure of the cylinder body.

As shown in FIG. 6, one valve recess 311 and two sector recesses 312 intersecting the upper cavity oil hole 361 and the lower cavity oil hole 362 are formed in the side wall of the cylinder body 31, so that hydraulic oil from the oil holes can flow into the sector recesses 312 without generating convection impact between channels in the staggered channel-type valve body; radius angles of the two sector recesses 312 are 55° and 150°, respectively.

Figure 7:
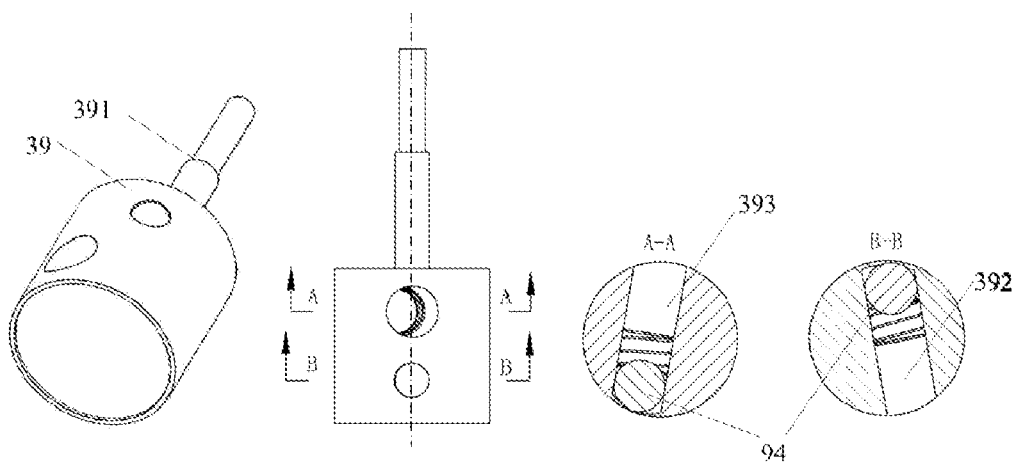
FIG. 7 is a schematic structural view and a sectional view of a staggered channel-type valve body according to an embodiment of this invention.

FIG. 7 is a schematic structural view and a sectional view of the staggered channel-type valve body.

As shown in FIG. 7, the staggered channel-type valve body 39 is provided with a first oil channel 392 and a second oil channel 393, and axes of the two oil channels are non-coplanar straight lines, so that the two oil channels do not influence each other and form an angle; the angle is configured such that the axes intersect at a point on an edge line of the staggered channel-type valve body at a pair of their ends and form an angle of 27.5° at the other pair of their ends when the axes of the two oil channels are projected on an end face of the staggered channel-type valve body; a circle of bulges is provided on either end face of the staggered channel-type valve body 39 to reduce a contact area of the valve body with the cylinder body 31 and the valve body sealing seat 310, respectively, and the valve body is placed in the valve recess 311; one-way valves 394 are provided in the first oil channel 392 and the second oil channel 393 in different directions, respectively.

As shown in FIGS. 3, 6, and 7, the DC servo motor 314 is geared with the motor-end bevel gear 316 through the valve body-end bevel gear 311 to adjust a rotation angle of the staggered channel-type valve body 39, flow areas of the two hydraulic oil channels in the valve body are changed through a fit clearance between either the first oil channel 392 or the second oil channel 393 in the valve body and the sector recess 312, so that a flow in the upper cavity and the lower cavity of the cylinder body are changed, and an angle sensor 312 is provided at a shaft end of the valve to enable complete closed-loop control of the motor.

Figure 8:
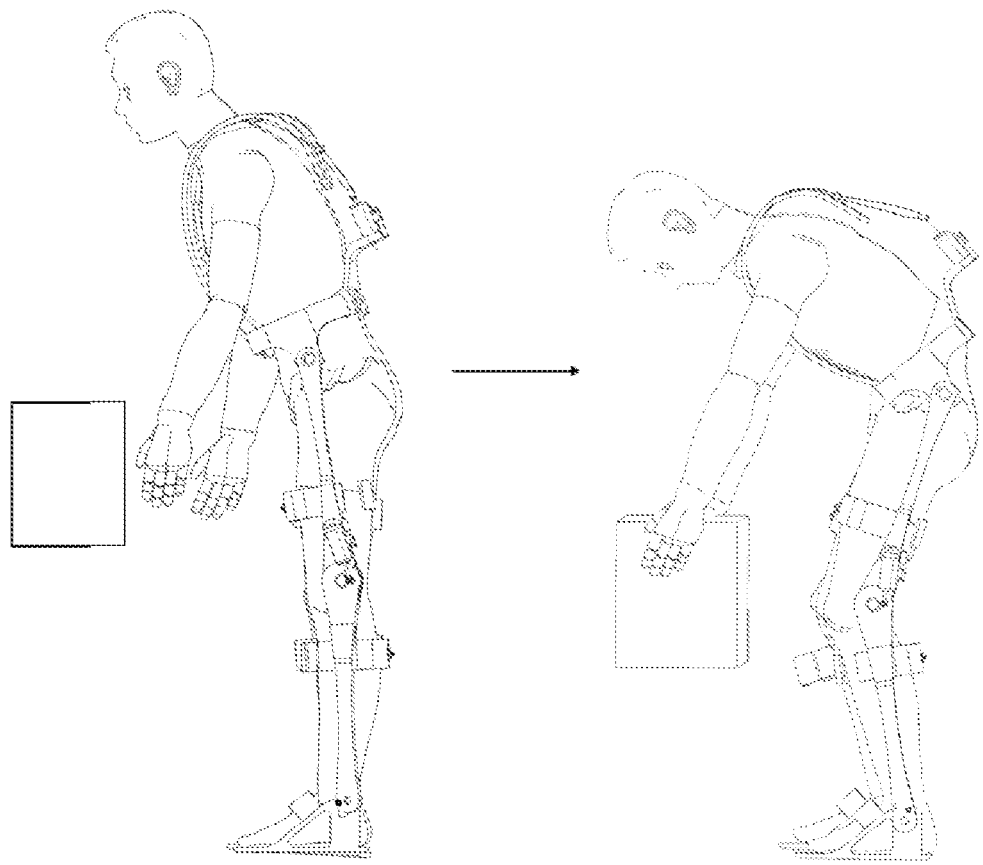
FIG. 8 is a schematic diagram illustrating a situation where a load is carried from a higher position to a lower position according to an embodiment of this invention.

FIG. 8 is a schematic diagram illustrating a situation where a load is carried from a higher position to a lower position.

As shown in FIG. 8, when a human body carries a load from a higher position to a lower position, the piston 34 in the waist hydraulic damping regulator 3b moves upwards under the action of gravity while the extension assisting spring 35 is compressed to store energy, hydraulic oil enters the hydraulic loop 36 through the upper cavity oil hole 362 to reach the sector recess 312, and the staggered channel-type valve body 39 is driven by the DC servo motor 314 to rotate to a preset angle, the one-way valve 394 in the second oil channel 393 closes, the flow area of hydraulic oil is changed by changing the area where the first oil channel 392 overlaps the sector recess 312, thereby providing variable damping force and dispersing the load on the waist of the human body to shoulders, the back and lower limbs, hence the active protection of the bones and muscles of the waist is enabled; when a human body stoops, the knee joint usually naturally bends, the piston 34 in the knee hydraulic damping regulator 3a moves upwards while the extension assisting spring 35 is compressed to store energy, similar to the waist hydraulic damping regulator, the flow area of hydraulic oil is changed by changing the area where the first oil channel 392 overlaps the sector recess 312, so that variable damping force is provided, and the effect of supporting the knee joint against a load is achieved.

Figure 9:
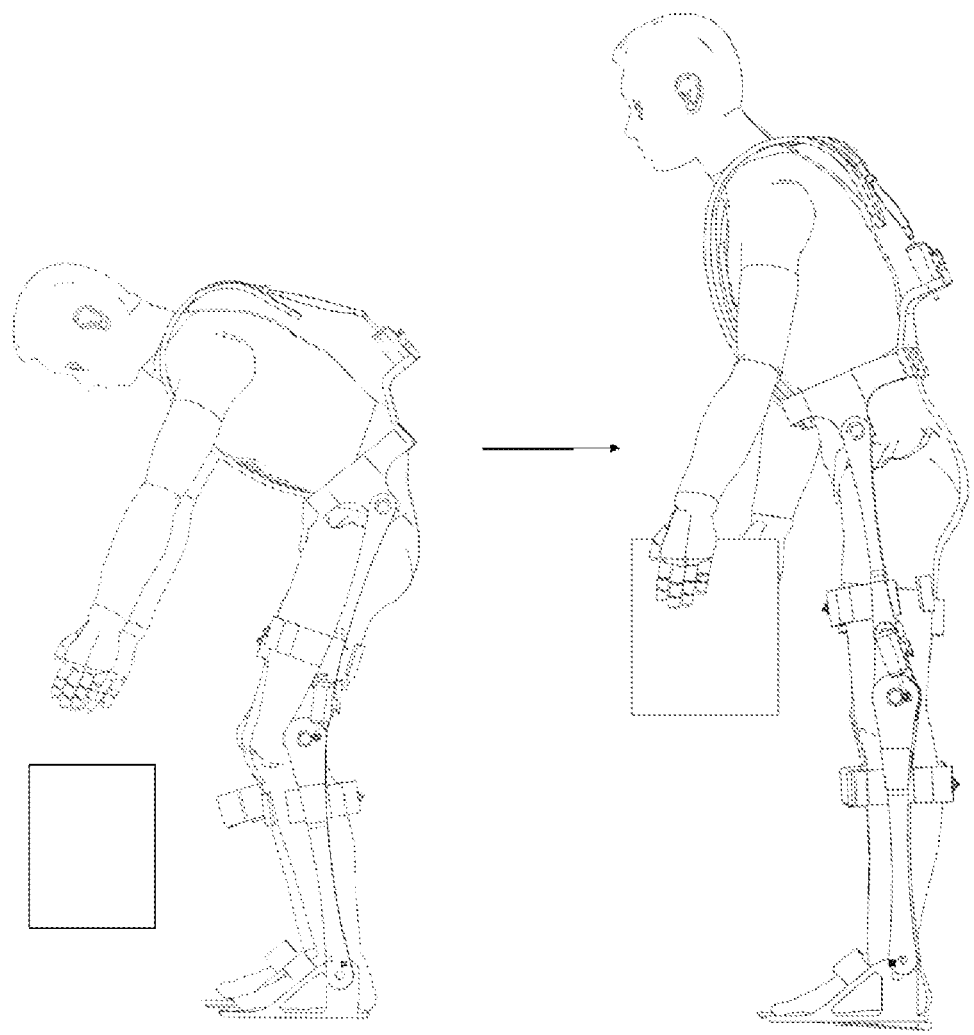
FIG. 9 is a schematic diagram illustrating a situation where a load is carried from a lower position to a higher position according to an embodiment of this invention.

FIG. 9 is a schematic diagram illustrating a situation where a load is carried from a lower position to a higher position.

As shown in FIG. 9, when the human body carries a load from a lower position to a higher position, the energy stored by the extension assisting spring 35 in the waist hydraulic damping regulator 3b is released, and the piston rod moves downwards to provide assistance for the waist when the human body stands up; the energy stored by the extension assisting spring 35 in the knee hydraulic damping regulator 3a is released, and the piston rod moves downwards to provide assistance for the extension of the knee joint.

Figure 10:
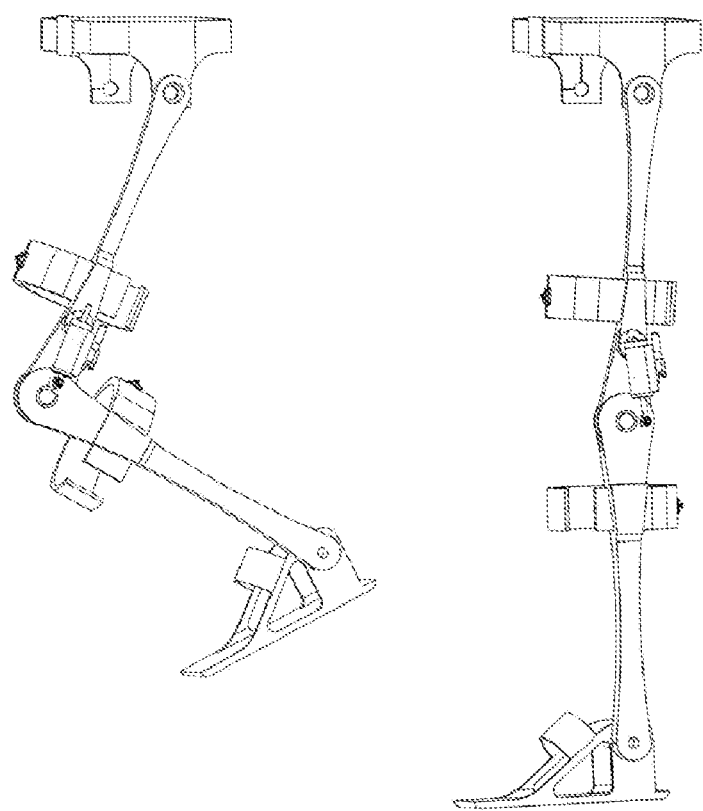
FIG. 10 is a schematic diagram illustrating a walking state according to an embodiment of this invention.

FIG. 10 is a schematic diagram illustrating a walking state.

As shown in FIG. 10, when the knee joint is in flexion during walking, the piston 34 moves downwards under the action of gravity, the extension assisting spring 35 is compressed to store energy, hydraulic oil enters the hydraulic loop 36 through the lower cavity oil hole 362 to reach the sector recess 320, the staggered channel-type valve body 39 rotates to a preset angle under the driving of the DC servo motor 314, the one-way valve 394 in the second oil channel 393 closes, and the flow area of the hydraulic oil is changed by changing the area where the first oil channel 392 overlaps the sector recess 320, so that the damping force borne by the knee joint during flexion is changed.

When the knee joint is in extension during walking, the energy stored by the extension assisting spring 35 is released to provide assistance for the upward movement of the piston 34, hydraulic oil enters the sector recess 312 through the lower cavity oil hole 361, the staggered channel-type valve body 39 rotates to a preset angle under the driving of the DC servo motor 314, the one-way valve 394 in the first oil channel 392 closes, and the flow area of the hydraulic oil is further changed by changing the area where the second oil channel 393 overlaps the sector recess 312, so that the damping force borne by the knee joint in extension is changed.

How the above embodiments work and their effects are as follows.

Normal workers in long-time repetitive labor may suffer prominent waist muscle and knee joint strain due to carrying loads and walking with loads for too long, which is harmful to physical health and reduces efficiency. The semi-active rigid-flexible coupling exoskeleton based on the single-loop bidirectional damping regulator supports two working modes, i.e., a heavy-object-carrying mode and a walking-with-load mode, and the heavy-object-carrying mode supports carrying from a higher to a lower position and the other way around. The waist and the back components are mainly made of flexible textile materials and elastic cables to construct a basic waist frame of the exoskeleton, and the basic waist frame is gently attached to a human body through optimized structures and stress positions; hydraulic dampers with a spring elastic structure are provided at the waist and the left and right knees, respectively, to provide assistance or damping force for the waist and the knees; the hydraulic damper can adjust bidirectional hydraulic oil flows through only one hydraulic oil loop by taking advantage of the design of a staggered channel-type valve body with a built-in one-way valve, wherein one channel is combined with an oil injection port, the number of openings of the hydraulic cylinder is minimized, the strength of the hydraulic cylinder is increased, and the possibility of oil leakage is reduced; by embedding the valve body in a side wall of the hydraulic cylinder, the difficulty in manufacturing and the oil leakage are further reduced; the bidirectional independent control of hydraulic damping is enabled by only one motor, and the damping regulation is continuous; compared with a hydraulic damping cylinder structure controlled by two motors, one motor control enables a smaller size, a reduced weight, and lower power consumption for the mechanism; the axial load acting on the motor in the damping cylinder can be effectively avoided, and the possibilities of motor out-of-step and damping regulation failure caused by an overlarge load are avoided; a large tangential force can be effectively prevented when the hydraulic oil flows out of the hydraulic oil channel and directly impacts the valve body in convection, the torque required by the motor for controlling the valve to rotate is greatly reduced, the power consumption is reduced, and the control performance of the motor is improved; the structure is delicate and easy to manufacture.

Preferred embodiments of this invention are described in detail above. It will be understood that numerous modifications and variations can be made following the concepts of this invention by those of ordinary skill in the art without involving any inventive effort. Therefore, all technical solutions which can be obtained by a person skilled in the art through logical analysis, reasoning, or limited experiments on the basis of the prior art according to the inventive concept of this invention shall fall within the scope defined by the claims.

The invention claimed is:

1. A semi-active rigid-flexible coupling exoskeleton based on a single-loop bidirectional damping regulator, characterized by comprising:
   a waist assembly and a leg assembly; and
   a hydraulic damping regulator comprising a cylinder body, a titanium alloy sleeve, a cylinder head, a piston, an extension assisting spring, an oil injection port plug, and a flow pre-regulating component, the flow pre-regulating component comprising a staggered channel-type valve body, a valve body sealing seat, a valve body-end bevel gear, an angle sensor, a motor fixing seat, a DC servo motor, a coupler, and a motor-end bevel gear;
   wherein,
   the titanium alloy sleeve is coaxially nested inside the cylinder body;
   the cylinder head is in threaded connection with an upper end of the cylinder body;
   the piston includes an upper piston rod, a piston body, and a hollow lower piston rod;
   the upper piston rod penetrates through the cylinder head;
   the hollow lower piston rod penetrates through a lower end of the cylinder body;
   the piston body moves up and down in the cylinder body and divides an inner cavity of the cylinder body into an upper cavity and a lower cavity;
   an upper cavity oil hole and a lower cavity oil hole are drilled into both ends of the inner cavity of the cylinder body correspondingly into the titanium alloy sleeve, respectively;
   an oil injection port is formed in a cylinder wall of the cylinder body, and an oil channel communicating the oil injection port with the upper cavity oil hole and the lower cavity oil hole forms a hydraulic oil circuit;
   the oil injection port plug is in threaded connection with the oil injection port;
   a special-shaped shaft is provided on one side of the staggered channel-type valve body;
   the special-shaped shaft is coaxially matched with a hole formed in the valve body sealing seat, the valve body-end bevel gear, and the angle sensor sequentially, and the valve body-end bevel gear is fixed with the angle sensor and the special-shaped shaft through a set screw;
   the valve body sealing seat and the motor fixing seat are fixed on a side wall of the cylinder body through screws;
   the DC servo motor is fixed on the motor fixing seat through threads, and an output end of the motor is connected with the motor-end bevel gear through the coupler; and
   the valve body-end bevel gear is geared with the motor-end bevel gear, wherein a valve recess and two sector recesses intersecting the upper cavity oil hole and the lower cavity oil hole are formed in the side wall of the cylinder body, so that hydraulic oil from the oil holes can flow into the sector recesses without generating convection impact between channels in the staggered channel-type valve body.

2. The semi-active rigid-flexible coupling hydraulic exoskeleton according to claim 1, characterized in that radius angles of the two sector recesses are 55° and 150°, respectively.

3. The semi-active rigid-flexible coupling hydraulic exoskeleton according to claim 1, characterized in that the staggered channel-type valve body is provided with a first oil channel and a second oil channel, and axes of the two oil channels are non-coplanar straight lines, so that the two oil channels do not influence each other and form an angle; the angle is configured such that the axes intersect at a point on an edge line of the staggered channel-type valve body at a pair of their ends and form an angle of 27.5° at the other pair of their ends when the axes of the two oil channels are projected on an end face of the staggered channel-type valve body; a circle of bulges is provided on either end face of the staggered channel-type valve body to reduce a contact area of the staggered channel-type valve body with the cylinder body and the valve body sealing seat, respectively, and the staggered channel-type valve body is placed in the valve recess; one-way valves are provided in the first oil channel and the second oil channel in different directions, respectively.

4. The semi-active rigid-flexible coupling hydraulic exoskeleton according to claim 3, characterized in that the DC servo motor is geared with the motor-end bevel gear through the valve body-end bevel gear to adjust a rotation angle of the staggered channel-type valve body, flow areas of the first oil channel and the second oil channel in the staggered channel-type valve body are changed through a fit clearance between either the first oil channel or the second oil channel in the staggered channel-type valve body and the sector recess, so that a flow in the upper cavity and the lower cavity of the cylinder body are changed, and an angle sensor is provided at a shaft end of the valve to enable complete closed-loop control of the DC servo motor.

5. A semi-active rigid-flexible coupling exoskeleton based on a single-loop bidirectional damping regulator, characterized by comprising:
- a waist assembly and a leg assembly; and
- a hydraulic damping regulator comprising a cylinder body, a titanium alloy sleeve, a cylinder head, a piston, an extension assisting spring, an oil injection port plug, and a flow pre-regulating component, the flow pre-regulating component comprising a staggered channel-type valve body, a valve body sealing seat, a valve body-end bevel gear, an angle sensor, a motor fixing seat, a DC servo motor, a coupler, and a motor-end bevel gear;
- wherein,
- the titanium alloy sleeve is coaxially nested inside the cylinder body;
- the cylinder head is in threaded connection with an upper end of the cylinder body;
- the piston includes an upper piston rod, a piston body, and a hollow lower piston rod;
- the upper piston rod penetrates through the cylinder head;
- the hollow lower piston rod penetrates through a lower end of the cylinder body;
- the piston body moves up and down in the cylinder body and divides an inner cavity of the cylinder body into an upper cavity and a lower cavity;
- an upper cavity oil hole and a lower cavity oil hole are drilled into both ends of the inner cavity of the cylinder body correspondingly into the titanium alloy sleeve, respectively;
- an oil injection port is formed in a cylinder wall of the cylinder body, and an oil channel communicating the oil injection port with the upper cavity oil hole and the lower cavity oil hole forms a hydraulic oil circuit;
- the oil injection port plug is in threaded connection with the oil injection port;
- a special-shaped shaft is provided on one side of the staggered channel-type valve body;
- the special-shaped shaft is coaxially matched with a hole formed in the valve body sealing seat, the valve body-end bevel gear, and the angle sensor sequentially, and the valve body-end bevel gear is fixed with the angle sensor and the special-shaped shaft through a set screw;
- the valve body sealing seat and the motor fixing seat are fixed on a side wall of the cylinder body through screws;
- the DC servo motor is fixed on the motor fixing seat through threads, and an output end of the motor is connected with the motor-end bevel gear through the coupler; and
- the valve body-end bevel gear is geared with the motor-end bevel gear, wherein the hydraulic damping regulator has two different structures corresponding to deployments at a waist and a knee, respectively namely, a knee hydraulic damping regulator and a waist hydraulic damping regulator, wherein the extension assisting spring in the knee hydraulic damping regulator is placed inside the lower cavity of the cylinder body, and the extension assisting spring in the waist hydraulic damping regulator is placed inside the upper cavity of the cylinder body, wherein the waist assembly comprises: a waist belt, a shoulder belt, a waist fixing seat, a piston rod connecting block, a pulley component, and a Bowden cable; the waist belt and the shoulder belt are made of flexible materials, and a front end of the shoulder belt passes around a human body to fixedly connect the waist belt; the waist belt fixing seat is made of a rigid material, and a lower end of the waist belt fixing seat is fixedly connected with the waist belt through a screw;
- the leg assembly comprises a thigh lever, a thigh strap, a leg lever connecting member, a shank lever, a shank strap, and a foot plate; an upper end of the thigh lever is coaxially connected with the lower end of the waist belt at a hip joint of the human body, so that the hip joint has freedom of rotation; the thigh strap penetrates through a square through hole formed in a middle end of the thigh lever for fixing the thigh lever and a thigh of the human body; the shank strap penetrates through a square through hole formed in a middle end of the shank lever for fixing the shank lever and a shank of the human body; a lower end of the shank lever is coaxially connected with the foot plate, so that an ankle joint has freedom of rotation, wherein in the waist assembly, the pulley component includes a pulley fixing seat, a first pulley, and a second pulley; the pulley fixing seat is fixed at a rear end of the shoulder belt through a screw; the first pulley and the second pulley are symmetrically arranged on two sides of an interior of the pulley fixing seat; the piston rod connecting block is coaxially connected with the upper piston rod in the waist hydraulic damping regulator, and the piston rod connecting block is provided with a first notch, the Bowden cable penetrates through the first notch of the piston rod connecting block and penetrates through the first pulley and the second pulley, respectively, to fixedly connect with left and right sides of the shoulder belt, respectively.

6. A semi-active rigid-flexible coupling exoskeleton based on a single-loop bidirectional damping regulator, characterized by comprising:
- a waist assembly and a leg assembly; and
- a hydraulic damping regulator comprising a cylinder body, a titanium alloy sleeve, a cylinder head, a piston, an extension assisting spring, an oil injection port plug, and a flow pre-regulating component, the flow pre-regulating component comprising a staggered channel-type valve body, a valve body sealing seat, a valve body-end bevel gear, an angle sensor, a motor fixing seat, a DC servo motor, a coupler, and a motor-end bevel gear;
- wherein,
- the titanium alloy sleeve is coaxially nested inside the cylinder body;
- the cylinder head is in threaded connection with an upper end of the cylinder body;
- the piston includes an upper piston rod, a piston body, and a hollow lower piston rod;
- the upper piston rod penetrates through the cylinder head;
- the hollow lower piston rod penetrates through a lower end of the cylinder body;

the piston body moves up and down in the cylinder body and divides an inner cavity of the cylinder body into an upper cavity and a lower cavity;

an upper cavity oil hole and a lower cavity oil hole are drilled into both ends of the inner cavity of the cylinder body correspondingly into the titanium alloy sleeve, respectively;

an oil injection port is formed in a cylinder wall of the cylinder body, and an oil channel communicating the oil injection port with the upper cavity oil hole and the lower cavity oil hole forms a hydraulic oil circuit;

the oil injection port plug is in threaded connection with the oil injection port;

a special-shaped shaft is provided on one side of the staggered channel-type valve body;

the special-shaped shaft is coaxially matched with a hole formed in the valve body sealing seat, the valve body-end bevel gear, and the angle sensor sequentially, and the valve body-end bevel gear is fixed with the angle sensor and the special-shaped shaft through a set screw;

the valve body sealing seat and the motor fixing seat are fixed on a side wall of the cylinder body through screws;

the DC servo motor is fixed on the motor fixing seat through threads, and an output end of the motor is connected with the motor-end bevel gear through the coupler; and the valve body-end bevel gear is geared with the motor-end bevel gear, wherein the hydraulic damping regulator has two different structures corresponding to deployments at a waist and a knee, respectively namely, a knee hydraulic damping regulator and a waist hydraulic damping regulator, wherein the extension assisting spring in the knee hydraulic damping regulator is placed inside the lower cavity of the cylinder body, and the extension assisting spring in the waist hydraulic damping regulator is placed inside the upper cavity of the cylinder body, wherein the waist assembly comprises: a waist belt, a shoulder belt, a waist fixing seat, a piston rod connecting block, a pulley component, and a Bowden cable; the waist belt and the shoulder belt are made of flexible materials, and a front end of the shoulder belt passes around a human body to fixedly connect the waist belt; the waist belt fixing seat is made of a rigid material, and a lower end of the waist belt fixing seat is fixedly connected with the waist belt through a screw;

the leg assembly comprises a thigh lever, a thigh strap, a leg lever connecting member, a shank lever, a shank strap, and a foot plate; an upper end of the thigh lever is coaxially connected with the lower end of the waist belt at a hip joint of the human body, so that the hip joint has freedom of rotation; the thigh strap penetrates through a square through hole formed in a middle end of the thigh lever for fixing the thigh lever and a thigh of the human body; the shank strap penetrates through a square through hole formed in a middle end of the shank lever for fixing the shank lever and a shank of the human body; a lower end of the shank lever is coaxially connected with the foot plate, so that an ankle joint has freedom of rotation, wherein in the leg assembly, the leg lever connecting member comprises a hydraulic cylinder rotary seat, a first end cover, a leg lever bearing, a second end cover, a third end cover, and a piston rod bearing; the hydraulic cylinder rotary seat is composed of a cylinder with a bulge and a hollow cylinder; the cylinder with the bulge is coaxially matched with the middle end of the thigh lever; the first end cover is fixed at a lower end of the thigh lever through a screw and axially fixes the hydraulic cylinder rotary seat through the bulge on the cylinder with the bulge; the hollow cylinder is fixedly connected with a bottom end of the knee hydraulic damping regulator; the hollow lower piston rod passes through the hollow cylinder to move up and down; a second notch is formed at an upper end of the shank lever, and the shank lever is installed in the second notch; the leg lever bearing is installed in a through hole in the lower end of the thigh lever and is coaxially matched with the upper end of the shank lever; the second end cover and the third end cover are fixed on left and right sides of a joint of the thigh lever and the shank lever through screws, respectively, to provide an axial fixation; a special-shaped shaft is provided at a rear part of the upper end of the shank lever, and a tail end of the special-shaped shaft is provided with a thread; the upper piston rod of the knee hydraulic damping regulator is coaxially matched with the special-shaped shaft through the piston rod bearing, and levers are axially fixed through the thread at the tail end of the special-shaped shaft and a nut.

\* \* \* \* \*